(12) United States Patent
Hallberg

(10) Patent No.: US 8,219,422 B2
(45) Date of Patent: Jul. 10, 2012

(54) TRICARE PAYMENT PROCESS

(75) Inventor: Charles Hallberg, Naples, FL (US)

(73) Assignee: MemberHealth, L.L.C., Solon, OH (US)

( * ) Notice: Subject to any disclaimer, the term of this patent is extended or adjusted under 35 U.S.C. 154(b) by 627 days.

(21) Appl. No.: 12/076,735

(22) Filed: Mar. 21, 2008

(65) Prior Publication Data

US 2008/0235050 A1   Sep. 25, 2008

Related U.S. Application Data

(60) Provisional application No. 60/907,137, filed on Mar. 22, 2007.

(51) Int. Cl.
*G06Q 40/00* (2012.01)
(52) U.S. Cl. .......................................................... 705/4
(58) Field of Classification Search ....................... 705/4
See application file for complete search history.

(56) References Cited

U.S. PATENT DOCUMENTS

| | | | |
|---|---|---|---|
| 6,249,774 B1 * | 6/2001 | Roden et al. | 705/28 |
| 2002/0002495 A1 * | 1/2002 | Ullman | 705/21 |

* cited by examiner

*Primary Examiner* — Charles Kyle
*Assistant Examiner* — Clifford Madamba
(74) *Attorney, Agent, or Firm* — NSIP Law

(57) ABSTRACT

An apparatus, a system, and a method are provided to pay a dispensing fee to a pharmacy and configured to replenish a pharmacy's inventory with prescription drugs by a wholesaler at no cost. Rather than being replenished for any prescription drug dispensed to a patient, a pharmacy would be paid a dispensing fee. To compensate for the wholesaler for replenishing the pharmacy at no cost, the wholesaler would receive an administrative fee. Furthermore, order rights are maintained for each participating pharmacy and wholesaler and monitor and record the transfer of order rights from a pharmacy to a wholesaler and the execute or the use by the wholesaler of the order rights. The order rights may include, in the alternative, a right assigned to the pharmacy to replenish the prescription drug dispensed or a different prescription drug for credit.

42 Claims, 9 Drawing Sheets

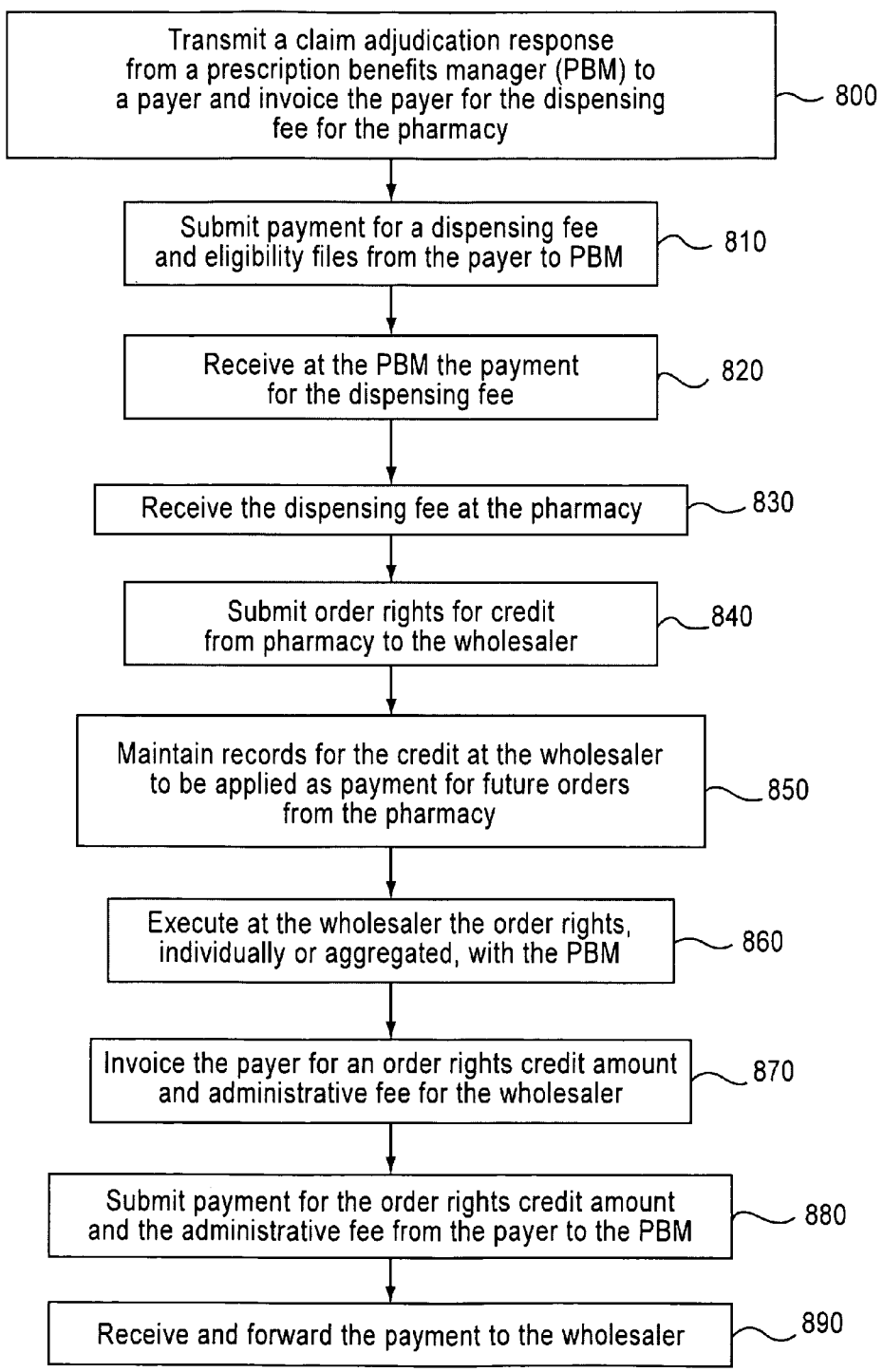

TRICARE PAYMENT PROCESS

CROSS REFERENCE TO RELATED APPLICATION

This application claims priority under 35 U.S.C. §119(e) of U.S. Provisional Patent Application Ser. No. 60/907,137, filed Mar. 22, 2007. The subject matter of the earlier filed application is hereby incorporated by reference.

BACKGROUND OF THE INVENTION

1. Field of the Invention

The present invention relates generally to an apparatus, a system, and a method of dispensing prescription drugs and information at a point-of-sale while incorporating aggregation of order rights, transferring of order rights from a pharmacy to a wholesaler, replenishing of prescription drugs, and allocating a dispensing fee to the pharmacy.

2. Description of the Related Art

Typically, individuals obtain medical services from health care providers. Such health care providers may include physicians, pharmacies, hospitals, or the like as needed. Increasingly, these services have received coverage by some form of third party payer, such as the employer, the government, or an insurance mechanism, with the balance payment remaining the responsibility of the patient. Sometimes the patient pays directly for the services, and sometimes payment is effected by use of credit through a credit card company or the like. At other times, claims are submitted by the patient or by the provider to an insurance company who then pays the provider, patient, or both, as appropriate.

The current retail drug distribution process requires the retail pharmacy to purchase drugs from wholesalers and to receive payment for the drugs from a benefits manager on behalf of the patient's insurer. The benefits manager then seeks payment from the drug manufacturer of rebates related to contracts between the benefits manager and the manufacturer.

However, an apparatus, a system, and a method are needed in which a pharmacy's inventory may be replenished by a wholesaler at no cost. To compensate a wholesaler for replenishing the pharmacy at no cost, the wholesaler would receive administrative fee. In addition, rather than being replenished for any prescription drugs dispensed to a patient, the pharmacy would be paid a dispensing fee. Furthermore, a prescription benefits manager is needed that would be able to maintain an order rights account for each participating pharmacy and wholesaler and monitor and record the execute and transfer of order rights from pharmacies to wholesalers.

Furthermore, an apparatus, a system, and a method are needed in which rather than being replenished for any prescription drugs dispensed to a patient, the pharmacy may elect to transfer the order rights to a wholesaler who originally supplied the prescription drugs dispensed or any other participating wholesaler for credit. A prescription benefits manager is needed that would be able to maintain order rights account for each participating pharmacy and wholesaler and monitor and record the transfer of order rights from pharmacies to wholesalers.

No prior art arrangements have provided an apparatus, a system, and a method for effectuating a fully integrated and cooperative system for dispensing and managing health care.

SUMMARY OF THE INVENTION

In accordance with an embodiment of the present invention, there is provided an apparatus including a receiver configured to receive and process a claim adjudication request, and a processor configured to grant an order right to a pharmacy based on the claim adjudication request. The order right includes a right assigned to the pharmacy to have a prescription drug dispensed replenished. The apparatus includes an output unit configured to output a claim adjudication response and the order right to a payer, and configured to output a dispensing fee to the pharmacy for dispensing a prescription drug to a patient, and a controller configured to execute the order right with a wholesaler to replenish the prescription drug dispensed to the pharmacy at no cost.

In accordance with an embodiment of the present invention, there is also provided an apparatus including a receiver configured to receive an order right from a pharmacy. The order right includes a right assigned to the pharmacy to have a prescription drug dispensed replenished. The apparatus includes a controller configured to replenish the pharmacy with the prescription drug dispensed at no cost to the pharmacy, and a processor configured to process the order right to invoice a prescription benefits manager for an administrative fee to compensate for replenishing the prescription drug to the pharmacy at no cost.

In accordance with an embodiment of the present invention, there is further provided a system including a prescription benefits manager configured to receive a claim adjudication request from a pharmacy for a prescription drug dispensed, output a claim adjudication response, and generate an assignment of order rights to the pharmacy based on the claim adjudication request, wherein the order rights include rights assigned to the pharmacy to have a prescription drug dispensed replenished. The system includes a wholesaler configured to receive the order rights from the pharmacy, aggregate the order rights up to order rights quantities, execute the aggregated order rights with the prescription benefits manager, and replenish the drugs to the pharmacy at no cost.

In accordance with an embodiment of the present invention, there is also provided a method including receiving and processing a claim adjudication request, granting an order right to a pharmacy based on the claim adjudication request. The order right includes a right assigned to the pharmacy to have a prescription drug dispensed replenished. The method includes outputting a claim adjudication response and the order right to a payer, outputting data representing a dispensing fee for the pharmacy for dispensing a prescription drug to a patient, and executing the order right with a wholesaler to replenish the prescription drug dispensed to the pharmacy at no cost.

In accordance with an embodiment of the present invention, there is further provided a method including receiving an order right from a pharmacy. The order right includes a right assigned to the pharmacy to have a prescription drug dispensed replenished. The method includes replenishing the pharmacy with the prescription drug dispensed at no cost to the pharmacy, and processing the order right to invoice a prescription benefits manager for an administrative fee to compensate a wholesaler for replenishing the prescription drug to the pharmacy at no cost.

In accordance with an embodiment of the present invention, there is also provided an apparatus including a receiver configured to receive and process a claim adjudication request, and a processor configured to grant an order right to a pharmacy based on the claim adjudication request. The order right includes a right assigned to the pharmacy to have a prescription drug dispensed replenished. The apparatus includes an output unit configured to output a claim adjudication response and an invoice to a payer for total charges of the order right. The total charges include an order right credit amount, an administrative fee for a wholesaler, and a dispensing fee to the pharmacy for dispensing the prescription drug. The order rights credit amount is an amount to be granted to the wholesaler for providing credit to the pharmacy for the order right. The apparatus includes a controller configured to transmit the administrative fee and order rights credit amount to the wholesaler.

In accordance with an embodiment of the present invention, there is further provided an apparatus including a receiver configured to receive an order right from a pharmacy. The order right includes a right assigned to the pharmacy to have a prescription drug dispensed replenished. A controller is configured to aggregate a predetermined number of order rights at predefined time intervals in predefined order quantities, configured to execute the aggregated order rights with a prescription benefits manager, and configured to provide the prescription drug requested by the pharmacy against the credit. A processor is configured to invoice the prescription benefits manager for the aggregated order rights associated with the dispensed orders from the pharmacy and for an administrative fee associated with the providing of the prescription drug to the pharmacy for credit.

In accordance with an embodiment of the present invention, there is further provided a system including a prescription benefits manager configured to receive a claim adjudication request from a pharmacy for a prescription drug dispensed, output a claim adjudication response, and generate an assignment of order rights to the pharmacy based on the claim adjudication request. The order rights include rights assigned to the pharmacy to have a prescription drug dispensed replenished. The system includes a wholesaler configured to receive the order rights from the pharmacy for credit in an amount equivalent to the amount of the order rights, aggregate the order rights up to order rights quantities, execute the aggregated order rights with the prescription benefits manager, and provide the prescription drug requested by the pharmacy against the credit.

In accordance with another embodiment of the present invention, there is provided a method including receiving and processing a claim adjudication request, granting an order right to a pharmacy based on the claim adjudication request. The order right includes a right assigned to the pharmacy to have a prescription drug dispensed replenished. The method includes outputting a claim adjudication response and an invoice to a payer for total charges of the order right. The total charges include an order right credit amount, an administrative fee for a wholesaler, and a dispensing fee to the pharmacy for dispensing the prescription drug. The order rights credit amount is an amount to be granted to the wholesaler for providing credit to the pharmacy for the order right. The method includes transmitting the administrative fee and order rights credit amount to the wholesaler.

In accordance with another embodiment of the present invention, there is provided a method including receiving an order right from a pharmacy. The order right includes a right assigned to the pharmacy to have a prescription drug dispensed replenished. The method includes aggregating a predetermined number of order rights at predefined time intervals in predefined order quantities, executing the aggregated order rights with a prescription benefits manager, providing the prescription drug requested by the pharmacy against the credit, and invoicing the prescription benefits manager for the aggregated order rights associated with the dispensed orders from the pharmacy and for an administrative fee associated with the providing of the prescription drug to the pharmacy for credit.

In accordance with an embodiment of the present invention, there is further provided a computer program embodied on a computer readable medium, the computer program being configured to control a processor to perform the method steps described above.

BRIEF DESCRIPTION OF THE DRAWINGS

Further embodiments, details, advantages and modifications of the present invention will become apparent from the following detailed description of the preferred embodiments which is to be taken in conjunction with the accompanying drawings, in which:

FIG. 11 illustrates an invoice and replenishing process, in accordance with an alternative embodiment of the present invention.

DETAILED DESCRIPTION OF THE PREFERRED EMBODIMENTS

Figure 1:
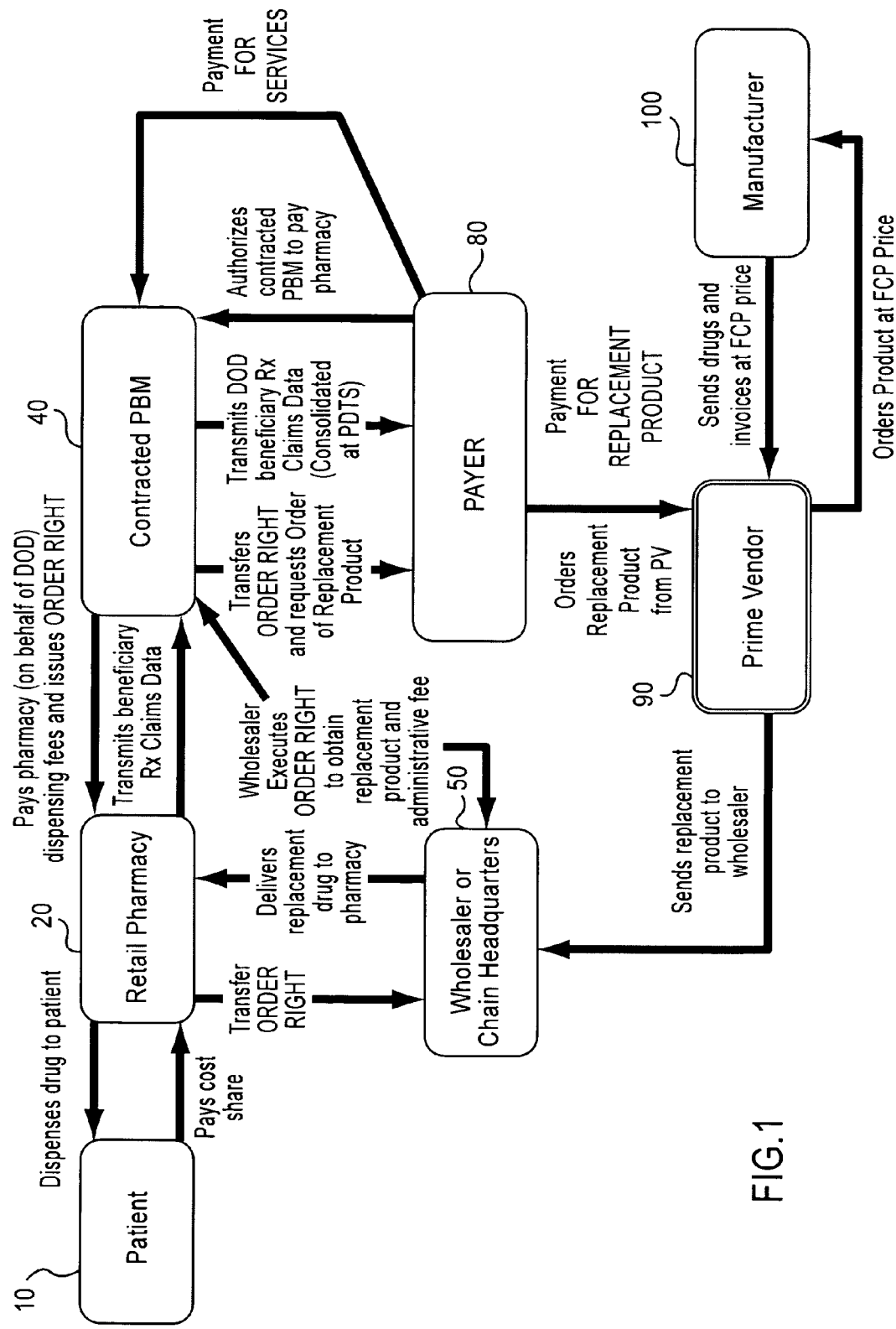
FIG. 1 is a schematic block diagram of a drug dispensing scheme, in accordance with an embodiment of the present invention.

Reference will now be made in detail to preferred embodiments of the present invention, examples of which are illustrated in the accompanying drawings.

TRICARE™ is the Department of Defense's health care program for members of the uniformed services, their families and survivors. TRICARE™ also offers health care programs for retired service members, including TRICARE™ Pharmacy, TRICARE™ Dental (United Concordia), and TRICARE™ for Life. In accordance with an exemplary embodiment of the present invention, an apparatus, a system, and a method described below may be applied to TRICARE™ health care program. However, a person of ordinary skill in the art will appreciate that the apparatus, system, and methods may be applied to other health care programs, with suitable modifications and equivalents, falling within the scope of the invention.

In accordance with an embodiment of the present invention, an apparatus, a system, and a method are provided configured to pay a dispensing fee to a pharmacy and configured to replenish a pharmacy's inventory with prescription drugs by a wholesaler at no cost. The apparatus, the system, and the method of the present invention would not require the pharmacy and/or a wholesaler to be replenished for the prescription drugs dispensed to patients.

Therefore, in accordance with an embodiment of the present invention, rather than being replenished for any prescription drug dispensed to a patient, a pharmacy would be paid a dispensing fee. To compensate for the wholesaler for processing order rights and replenishing the pharmacy at no cost, the wholesaler may receive an administrative fee. Furthermore, a health provider (PBM), in accordance with an embodiment of the present invention would be configured to maintain an order rights account for each participating pharmacy and wholesaler and monitor and record the transfer of order rights from a pharmacy to a wholesaler and the execute or the use by the wholesaler of the order rights.

In accordance with an embodiment of the present invention, an order right is a right assigned by a healthcare provider to a pharmacy as a guaranty to replenish of a prescription drug that was dispensed.

In accordance with an embodiment of the present invention, the pharmacy may aggregate all order rights associated with a particular wholesaler, in appropriate order quantities, and transfer the aggregated order rights to the particular wholesaler who will executes the order rights with the healthcare provider and supply or replenish the prescription drugs to the pharmacy at no cost. In an alternative embodiment of the present invention, the pharmacy may elect to transfer the order rights to the wholesaler for credit. The wholesaler would give the pharmacy credit in an amount equivalent to the aggregated amount of the order rights. In accordance with an embodiment of the present invention, the order right is a right assigned to the pharmacy to receive credit for a prescription drug dispensed.

The present system combines electronic hardware and software components to create an apparatus, a system, and a method of dispensing prescription drugs and information at a point-of-sale while incorporating data management of tracking order rights, drug replenishing process, and allocating a dispensing fee to the pharmacy.

FIG. 1 is a schematic block diagram of a drug dispensing scheme, in accordance with an embodiment of the present invention. The system and each subsystem or apparatus disclosed and described in FIG. 1 achieves integration of data management into the payment process by providing a communication network that allows each of its subsystems, operatively connected with each other, to send and receive information. For example, a pharmacy, a chain headquarters, and a prescription benefits manager (PBM) or healthcare provider, such as MEMBERHEALTH™, may be responsible for collecting patient information and distributing or making it available to other subsystems. In one instance, the patient information obtained from the pharmacy and the chain headquarters subsystems may be used by the PBM to process claim adjudications and manage order rights. The PBM could grant order rights to the pharmacy to enable replenishing of a prescription drug that was dispensed without costs to the pharmacy, in accordance with an embodiment of the present invention. The pharmacy would also receive a dispensing fee for dispensing prescription drugs to a patient. In accordance with an embodiment of the present invention, the dispensing fee may be an amount associated with the dispensing of a single prescription or an amount associated with the dispensing of a plurality of prescriptions.

The system of FIG. 1 includes a pharmacy 20, a contracted prescription benefits manager (PBM) 40, a wholesaler or a chain headquarters 50, a payer 80, such as the Department of Defense (DoD) provider book only (PBO)/TRICARE™ management activity (TMA), a prime vendor 90, and a manufacturer 100 subsystems. A patient 10 submits a prescription to a pharmacy 20. The pharmacy 20 then issues a claim adjudication request to the PBM 40 for the prescription drug (s) dispensed to the patient 10. A claim adjudication request refers to a request for a determination of a patient's payment, or financial responsibility, after a medical claim is applied to the patient's insurance benefits. The claim adjudication, in accordance with an embodiment of the present invention, may be done in real time, which would be a process that would instantaneously adjudicate a claim before the patient even leaves the pharmacy 20.

The PBM 40, in turn, receives and processes the claim adjudication request and outputs a claim adjudication response back to the pharmacy 20 detailing total charges associated with the prescription drug dispensed including a patient's co-pay, which is a specified dollar amount that the patient is required to pay to cover his/her portion of the cost for medication cost, if any, and a dispensing fee for the pharmacy 20 for dispensing the prescription drugs. The PBM 40 also issues or grants order rights to the pharmacy 20.

In addition, the pharmacy 20 receives the claim adjudication response and the order rights from the PBM 40 and directs the patient 10 to pay the co-pay, if any, and dispenses the prescription drug to the patient 10.

As shown in FIG. 1, because the wholesaler 50 may be operatively connected to multiple pharmacies, in order to be able to associate the dispensing fee with the corresponding pharmacy 20, the dispensing fee may be provided with a national council for prescription drug programs (NCPDP) format associating the dispensing fee to the corresponding pharmacy 20. The dispensing fee may be a total amount for the aggregated order rights corresponding to the particular pharmacy 20. Therefore, in accordance with an embodiment of the present invention, rather than being replenished for the prescription drugs dispensed to a patient 10, the pharmacy 20 is paid the dispensing fee.

Furthermore, upon dispensing the prescription drug to the patient 10, the pharmacy 20 may elect to aggregate a predetermined number of order rights either at predefined time intervals, associated with a particular wholesaler, a predetermined number of patients, or in predefined order quantities. The pharmacy 20 may then transfer the aggregated order rights to the wholesaler 50, who will execute the order rights with the PBM 40 and supply or replenish the drugs to the pharmacy 20 at no cost. The predefined order quantities may include an aggregated number of prescription drugs dispensed.

Specifically, the pharmacy 20 may transfer, as a batch, the aggregated order rights to the wholesaler 50 for the drugs dispensed, and replenished by the wholesaler 50. The wholesaler 50 may further aggregate the order rights up to order rights quantities. The wholesaler 50 executes or uses the order rights. To compensate for the wholesaler for replenishing the pharmacy at no cost, the wholesaler may receive an administrative fee. Therefore, the wholesaler 50 may invoice the PBM 40 for the administrative fee.

Furthermore, upon dispensing the prescription to the patient 10, the PBM 40 transmits the claim adjudication response to the payer 80. Also, the PBM 40 transfers the order rights and invoices the payer 80 for the total charges for processing the aggregated order rights, including the administrative fee for the wholesaler 50 and the dispensing fee for the pharmacy 20 associated with the claim adjudication response. In the transfer of the order rights, the PBM 40 provides information, such as quantity of the drugs dispensed based on the aggregated order rights and identification of the wholesaler 50, to the payer 80.

In response, the payer 80 submits the payment for the total charges to PBM 40 and transmits eligibility files to the PBM 40. The PBM 40 receives the payment for the total charges from the payer 80. The PBM 40 would then transmit the administrative fee to the wholesaler 50.

In accordance with an embodiment of the present invention, the payer 80 may provide ordering and sorting of the information, such the quantity of the drugs dispensed and the identification of the wholesaler 50 that will be replenished by a drug manufacturer. The payer 80 may order the prime vendor 90 to replenish the quantity of the drugs dispensed to the wholesaler 50. The payer 80 also submits to the prime vendor 90 payment for the quantity of drugs to be replenished. In accordance with an alternative embodiment of the present invention, the system may exclude the prime vendor 90 and the payer 80 may directly order the manufacturer 100 to replenish the quantity of prescription drugs dispensed. If the system includes the prime vendor 90 and the manufacturer 100, upon receiving the order from the payer 80, the prime vendor 90 orders the prescription drugs from the manufacturer 100 at federal ceiling prices (FCP), for instance. The manufacturer 100 sends the prescription drugs to the prime vendor 90 and invoices the prime vendor 90 at the FCP prices.

The prime vendor 90 or, if the prime vendor 90 is not included, the manufacturer 100 would then replenish the wholesaler 50 with the drugs. The wholesaler 50 would replenish the pharmacy's 20 inventory at no cost. In accordance with an embodiment of the present invention, the pharmacy 20 may request that the replenishment be done at a later time rather than upon the time the prime vendor 90 provides the drugs to the wholesaler 50. Although not shown, the PBM 40 may invoice a TRICARE™ management activity (TMA) for reimbursement of administrative fee paid to the wholesaler 50.

Figure 2:
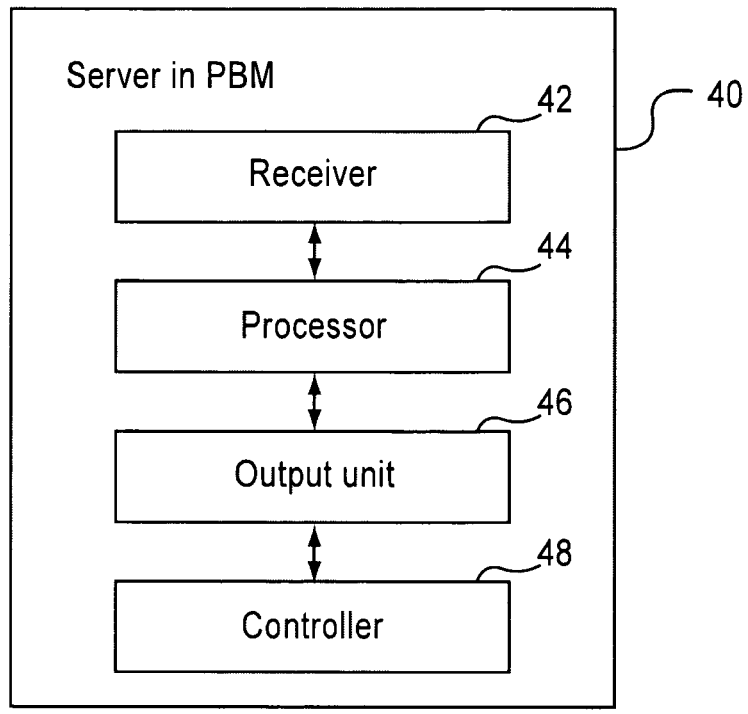
FIG. 2 illustrates a server in a prescription benefits manager, in accordance with an embodiment of the present invention.

FIG. 2 illustrates a server in the PBM 40, in accordance with an embodiment of the present invention. The server may include, as shown in FIG. 2, a receiver 42 configured to receive and process a claim adjudication request. The receiver 42 is further configured to receive an invoice from the wholesaler 50 for an administrative fee for replenishing the prescription drug to the pharmacy 20 at no cost. Based on the claim adjudication request, a processor 44 is configured to grant an order right to a pharmacy 20. The order right includes a right assigned to the pharmacy 20 to have a prescription drug dispensed replenished. An output unit 46 is configured to output a claim adjudication response and data representing a dispensing fee for the pharmacy 20 for dispensing a prescription drug. The output unit 46 is further configured to transmit the order rights and an invoice to the payer 80 for total charges of the order right. The total charges include data representative of the administrative fee for the wholesaler 50 and the data representing the dispensing fee. The receiver 42 is then configured to receive a payment for the total charges and eligibility files from the payer 80. A controller 48 is configured to execute the order right with a wholesaler 50 to replenish the prescription drug dispensed to the pharmacy 20 at no cost.

Figure 3:
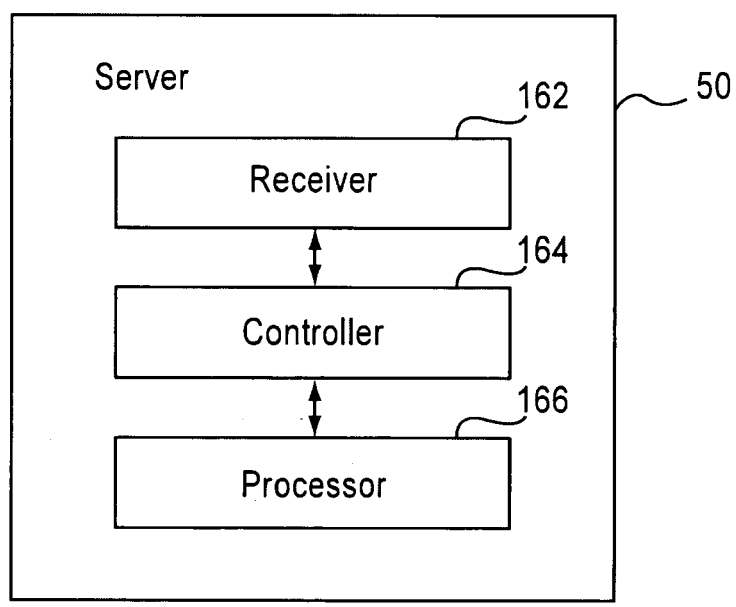
FIG. 3 illustrates a server in a wholesaler, in accordance with an embodiment of the present invention.

FIG. 3 illustrates a server in a wholesaler 50, in accordance with an embodiment of the present invention. The server includes a receiver 162 configured to receive an order right from a pharmacy 20. The order right includes a right assigned to the pharmacy 20 to have a prescription drug dispensed replenished. A controller 164 is configured to aggregate a predetermined number of order rights at predefined time intervals in predefined order quantities. The controller 164 is further configured to replenish the pharmacy 20 with the same prescription drug dispensed at no cost to the pharmacy 20. A processor 166 in the server is configured to process the order right to invoice a PBM 40 for an administrative fee to compensate the wholesaler 50 for replenishing the prescription drug to the pharmacy 20 at no cost.

Figure 4:
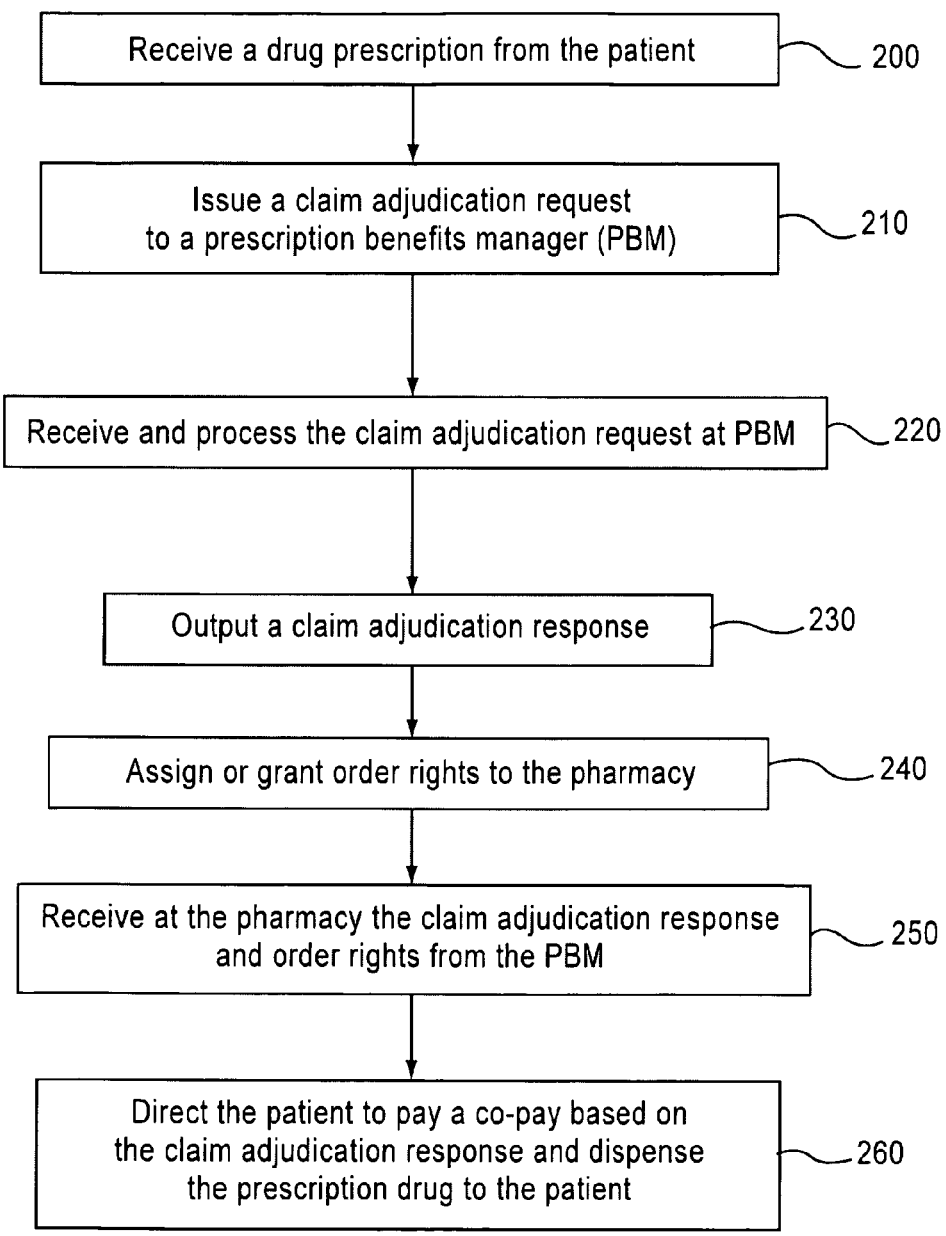
FIG. 4 illustrates an order rights process, in accordance with an embodiment of the present invention.

FIG. 4 illustrates an order rights process in which a healthcare provider (PBM) assigns an order right to a pharmacy to enable replenishing of a dispensed prescription drug, in accordance with an embodiment of the present invention. At step 200, the pharmacy 20 receives a drug prescription from the patient 10. At step 210, the pharmacy 20 issues a claim adjudication request to bill for the prescription drug(s) to be dispensed to the prescription benefits manager (PBM) 40. At step 220, the PBM 40 receives and processes the claim adjudication request. At step 230, the PBM 40 outputs a claim adjudication response detailing total charges associated with the prescription drug dispensed including the patient's co-pay. At step 240, the PBM 40 may also assign or grant order rights to the pharmacy 20. At step 250, the pharmacy 20 receives the claim adjudication response and order rights from the PBM 40. At step 260, the pharmacy 20 directs the patient 10 to pay a co-pay based on the claim adjudication response, if required, and dispenses the prescription drug to the patient 10.

Figure 5:
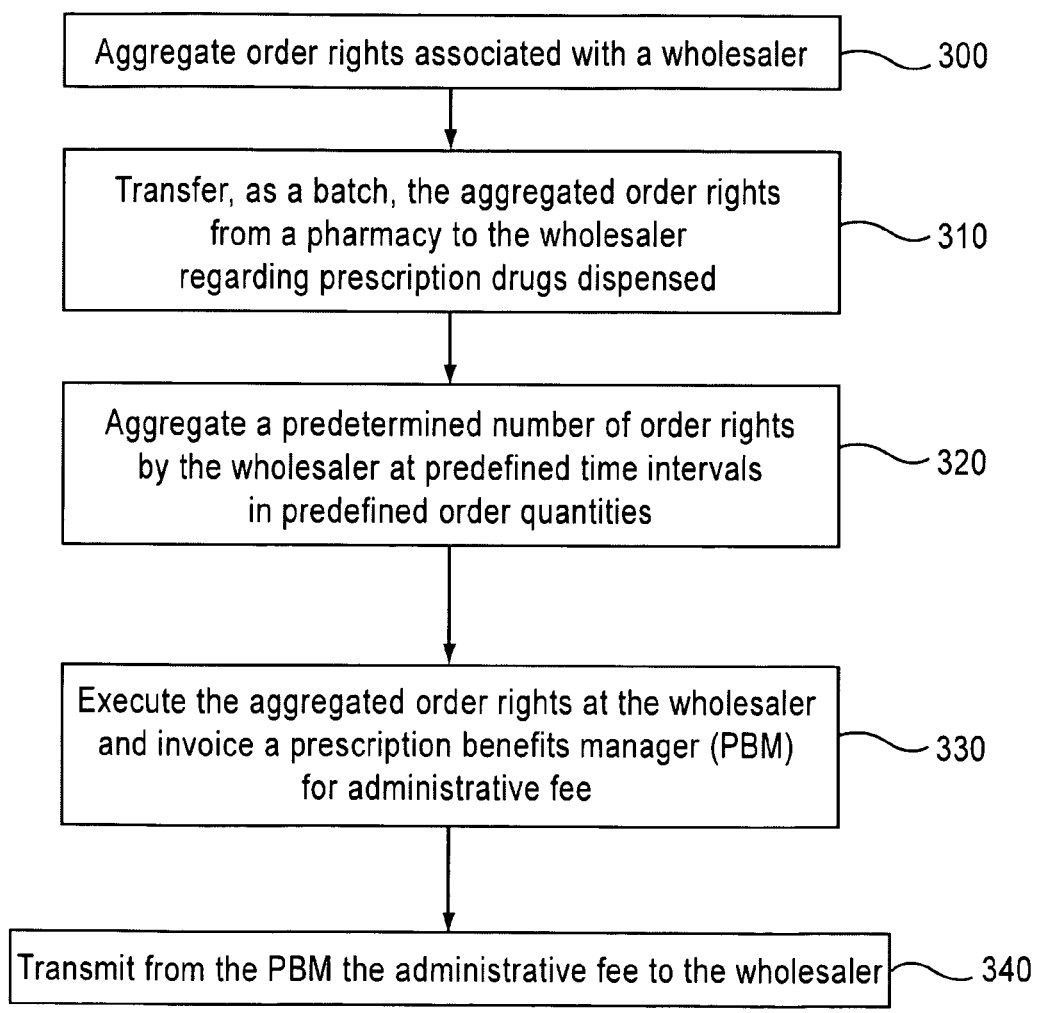
FIG. 5 illustrates an aggregated order rights process, in accordance with an embodiment of the present invention.
Figure 6:
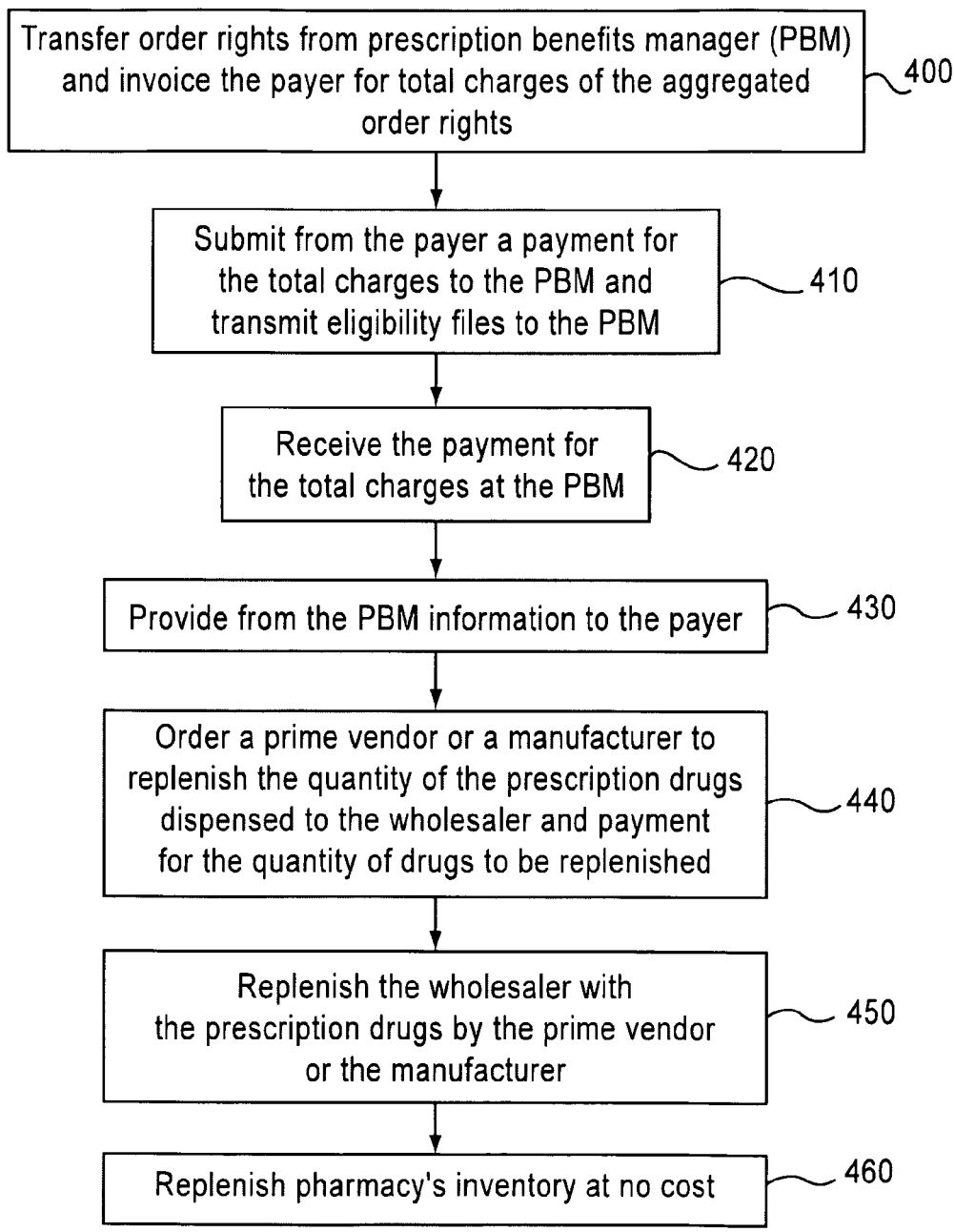
FIG. 6 illustrates a replenishing process, in accordance with an embodiment of the present invention.

After step 260, the processes illustrated and described in FIGS. 5 and 6 may be executed or performed simultaneously or sequentially.

FIG. 5 illustrates an aggregated order rights process, in accordance with an embodiment of the present invention. Upon dispensing the prescription to the patient 10 (after step 260 in FIG. 4), at step 300, the pharmacy 20 may elect to aggregate all order rights associated with a particular wholesaler 50, in appropriate order quantities, and transfer the aggregated order rights to the particular wholesaler 50, who will execute the order rights with the PBM 40 and supply or replenish the prescription drugs to the pharmacy 20 at no cost. Therefore, at step 310, the pharmacy 20 may transfer, as a batch, the aggregated order rights to the wholesaler 50 regarding prescription drugs dispensed associated with the wholesaler 50. At step 320, the wholesaler 50 may be configured to aggregate a predetermined number of order rights at predefined time intervals in predefined order quantities. At step 330, the wholesaler 50 executes or uses the aggregated order rights and invoices the PBM 40 for administrative fee to compensate the wholesaler 50 for replenishing the prescription drug to the pharmacy 20 at no cost. At step 340, the PBM 40 transmits the administrative fee to the wholesaler 50.

FIG. 6 illustrates a replenishing process, in accordance with an embodiment of the present invention. Upon dispensing the prescription to the patient 10 (after step 260 of FIG. 4), at step 400, the PBM 40 transfers the order rights and invoices the payer 80 for the total charges of the aggregated order rights, including the administrative fee for the wholesaler 50 and the dispensing fee for the pharmacy 20 associated with the claim adjudication response. At step 410, the payer 80 submits the payment for the total charges to the PBM 40 and transmits eligibility files to the PBM 40. At step 420, the PBM 40 receives the payment for the total charges from the payer 80 with authorization to pay the dispensing fee to the pharmacy 20 and the administrative fee to the wholesaler 50.

At step 430, the PBM 40 provides information, such as quantity of the prescription drugs dispensed based on the aggregated order rights and identification of the wholesaler 50, to the payer 80. At step 440, the payer 80 orders the prime vendor 90 or the manufacturer 100 to replenish the quantity of the prescription drugs dispensed to the wholesaler 50. The payer 80 also submits to the prime vendor 90 or the manufacturer 100 payment for the quantity of drugs to be replenished.

In accordance with an alternative embodiment of the present invention, the prime vendor 90 or the manufacturer 100 may instead replenish the wholesaler 50 with prescription drugs through a direct purchase or payment from the payer 80. At step 450, the prime vendor 90 or the manufacturer 100 replenishes the wholesaler 50 with the prescription drugs. At step 460, the wholesaler 50 replenishes the pharmacy's 20 inventory at no cost.

Therefore, in accordance with an embodiment of the present invention, rather than being replenished for any prescription drugs dispensed to a patient, a pharmacy is paid a dispensing fee. The pharmacy's inventory is replenished by the wholesaler at no cost. Furthermore, to compensate a wholesaler for replenishing the pharmacy at no cost, the wholesaler would receive administrative fee. A health provider (such as, PBM), in accordance with an embodiment of the present invention, may maintain an order rights account for each participating pharmacy and wholesaler and monitor and record the execute and transfer of order rights from pharmacies to wholesalers.

In accordance with an embodiment of the present invention, rather than being replenished for any prescription drugs dispensed to a patient, the pharmacy may elect to transfer the order rights to a wholesaler who originally supplied the prescription drugs dispensed or any other participating wholesaler for credit through a health provider (PBM) in an amount equivalent to an aggregated amount of the order rights. Furthermore, in accordance with an aspect of the present invention, the pharmacy may have the option of either requesting the wholesaler who originally supplied the prescription drugs dispensed or another participating wholesaler to replenish the pharmacy's inventory with the same prescription drug or prescription drugs dispensed.

Figure 7:
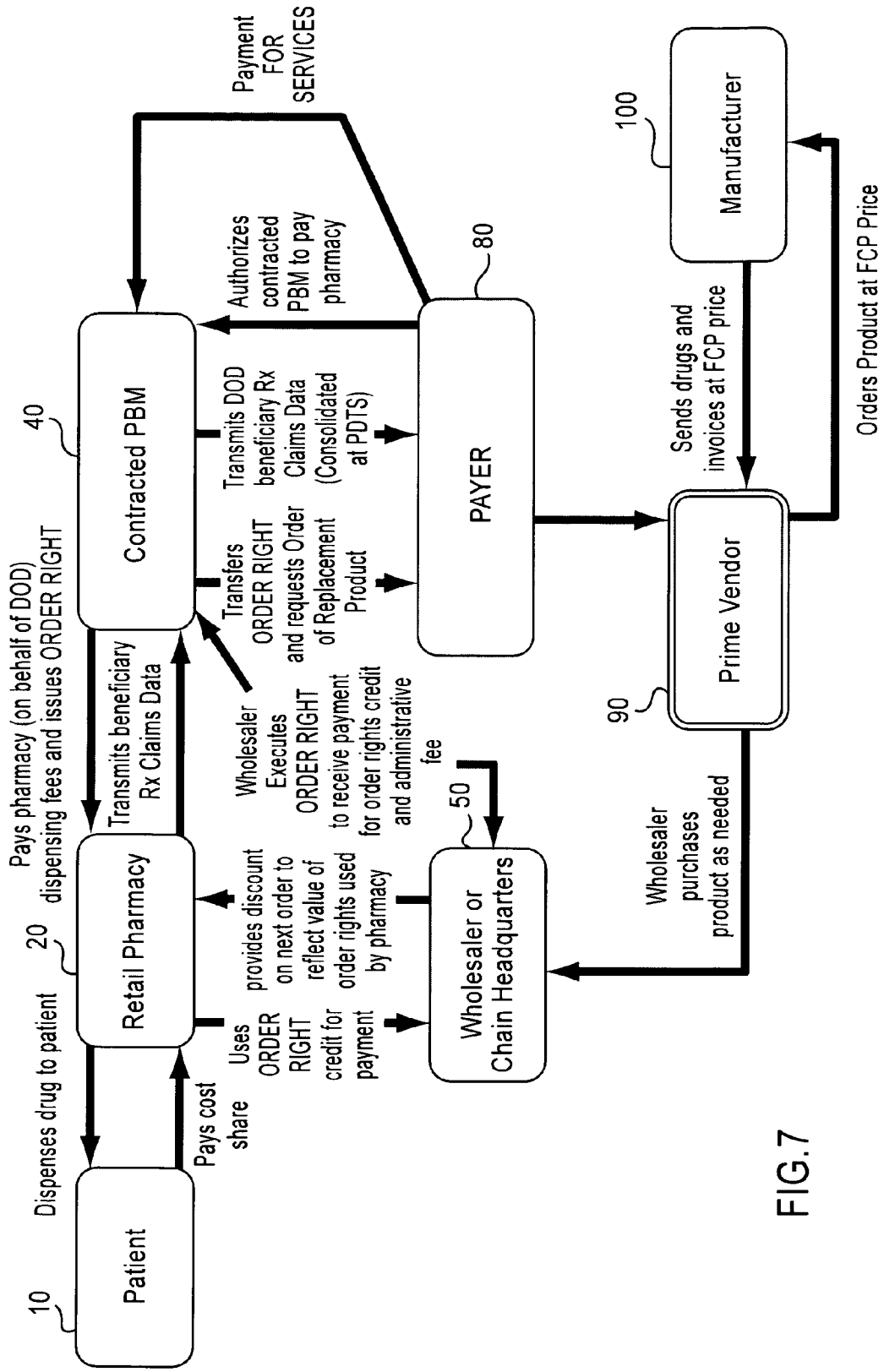
FIG. 7 is a schematic block diagram of a drug dispensing scheme, in accordance with an alternative embodiment of the present invention.

FIG. 7 is a schematic block diagram of a drug dispensing scheme, in accordance with an alternative embodiment of the present invention. Rather than being replenished for any prescription drugs dispensed to a patient, the pharmacy 20 may elect to transfer the order rights to a wholesaler 50 who originally supplied the prescription drugs dispensed or any other participating wholesaler 50 for credit through the health provider (PBM) 40 in an amount equivalent to an aggregated amount of the order rights. Furthermore, in accordance with an aspect of the present invention, the pharmacy 20 may have the option to request the wholesaler 50 to provide other prescription drug(s) that the wholesaler 50 may distribute.

Therefore, in the order rights system of FIG. 7, after the patient 10 submits a drug prescription to a pharmacy 20, the pharmacy 20 would issue a claim adjudication request to bill for the prescription drug(s) dispensed. The PBM 40 receives and processes the claim adjudication request and outputs a claim adjudication response back to the pharmacy 20 detailing total charges associated with the prescription drug dispensed including a patient's co-pay, if any, and a dispensing fee for the pharmacy for dispensing the prescription drugs. The PBM 40 also assigns or grants order rights to the pharmacy 20.

In addition, the pharmacy 20 receives the claim adjudication response and the order rights from the PBM 40 and directs the patient 10 to pay the co-pay, if any, and dispenses the prescription drug to the patient 10.

Upon dispensing the prescription drug to the patient 10, the pharmacy 20 may elect to aggregate a predetermined number of order rights either at predefined time intervals, associated with a particular wholesaler, a predetermined number of patients, or in predefined order quantities. The pharmacy 20 may transfer the order rights to the wholesaler or chain headquarters 50 for credit in an amount equivalent to the aggregated amount of the order rights. In accordance with another embodiment of the present invention, the pharmacy 20 may elect to use the order rights as credit as a payment with any participating wholesaler 50.

In accordance with an alternative embodiment of the present invention, the pharmacy 20 may request prescription drugs dispensed or with other prescription drugs that the wholesaler 50 may provide.

The wholesaler 50 may further aggregate the order rights up to order rights quantities. Also, the wholesaler 50, executes or uses the order rights with the PBM 40 and provides the prescription drug(s) requested by the pharmacy 20 against the credit. The wholesaler 50 executes or uses the order rights and invoices the PBM 40 for the entire order rights associated with the dispensed orders from the pharmacy 20. The wholesaler 50 may also invoice the PBM 40 for the administrative fee associated with the replacement of prescription drugs to the pharmacy 20 for credit.

Furthermore, the PBM 40 transmits the claim adjudication response to the payer 80. Also, the PBM 40 transfers the order rights and invoices the payer 80 for the total charges of the aggregated order rights, including order rights credit amount, the administrative fee for the wholesaler 50, and the dispensing fee for the pharmacy 20 associated with the claim adjudication response. The order rights credit amount is an amount to be granted to the wholesaler 50 for providing credit to the pharmacy 20 for the order rights. In response, the payer 80 submits the payment for the total charges to PBM 40 and transmits eligibility files to the PBM 40. The PBM 40 receives the payment for the total charges from the payer 80 with an authorization to pay the dispensing fee to the pharmacy 20. The PBM 40 would then transmit the administrative fee and order rights credit amount to the wholesaler 50.

In the transfer of the order rights, the PBM 40 may provide information, such as quantity of the drugs dispensed based on the aggregated order rights and identification of the wholesaler 50, to the payer 80. The wholesaler 50 would purchase products from the prime vendor 90 or the manufacturer 100 as needed.

Figure 8:
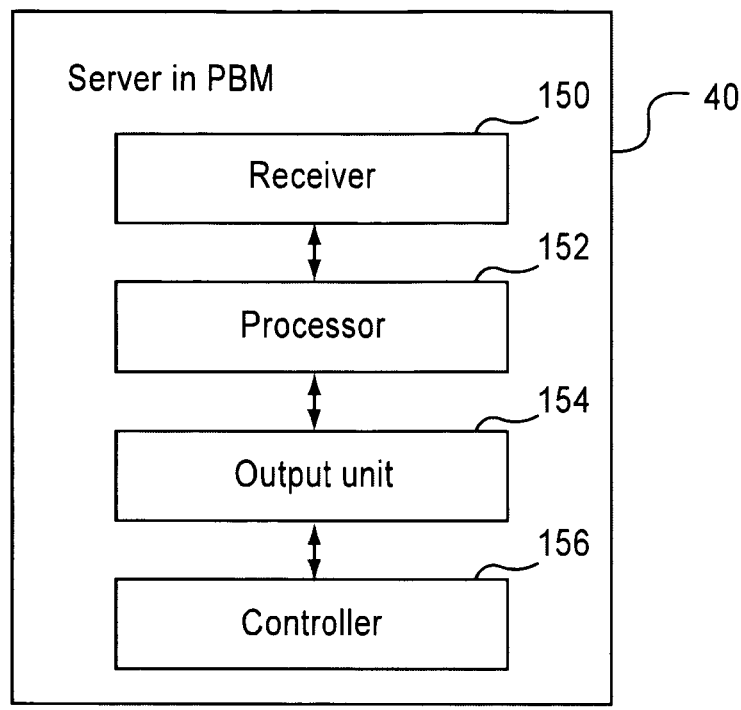
FIG. 8 illustrates a server in a prescription benefits manager, in accordance with an alternative embodiment of the present invention.

FIG. 8 illustrates a server in the PBM 40, in accordance with an alternative embodiment of the present invention. The server may include a receiver 150 configured to receive and process a claim adjudication request. Based on the claim adjudication request, a processor 152 is configured to grant the order right to the pharmacy 20. An output unit 154 is configured to output a claim adjudication response and the order right to the payer 80 and the dispensing fee for the pharmacy 20 for dispensing the prescription drug.

A controller 156 is configured to execute the order right with the wholesaler 50 to provide the prescription drug dispensed or another prescription drug to the pharmacy 20 against the credit. The controller 156 processes the claim adjudication request in real time.

The output unit 154 transmits the claim adjudication response to the payer 80. The output unit 154 is further configured to transmit an invoice to the payer 80 for total charges of the order right. The total charges include the order right credit amount, the administrative fee for the wholesaler 50, and the data representing the dispensing fee. As previously described, the order rights credit amount is an amount to be granted to the wholesaler 50 for providing credit to the pharmacy 20 for the order rights. The receiver 150 is configured to receive a payment for the total charges and eligibility files from the payer 80. Upon receipt of the administrative fee and the order rights credit amount from the payer 80, the output unit 154 would transfer the administrative fee and the order rights credit amount to the wholesaler 50.

Figure 9:
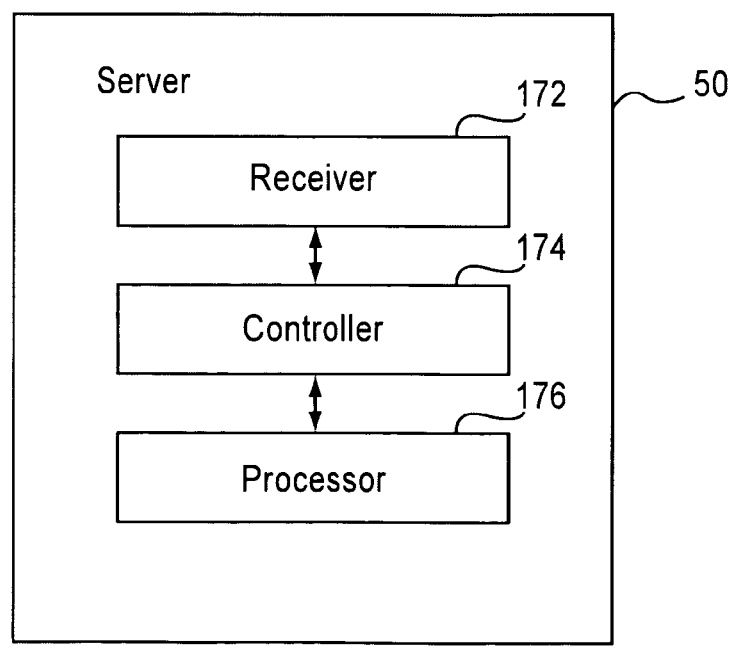
FIG. 9 illustrates a server in a wholesaler, in accordance with an alternative embodiment of the present invention.

FIG. 9 illustrates a server in a wholesaler 50, in accordance with an embodiment of the present invention. The server includes a receiver 172 configured to receive the order rights from the pharmacy 20 for credit. A controller 174 is configured to aggregate a predetermined number of order rights at predefined time intervals in predefined order quantities. A controller 174 executes or uses the order rights with the PBM 40 and provides the prescription drug(s) requested by the pharmacy 20 against the credit. A processor 176 invoices the PBM 40 for the entire order rights associated with the dispensed orders from the pharmacy 20. The processor 176 may also invoice the PBM 40 for the administrative fee associated with the replacement of prescription drugs to the pharmacy 20 for credit.

For the order rights system illustrated in FIG. 7, the order rights process in which a healthcare provider (PBM 40) assigns the order right to a pharmacy to enable replenishing of a prescription drug that was dispensed as illustrated and described for FIG. 4 are repeated.

Figure 10:
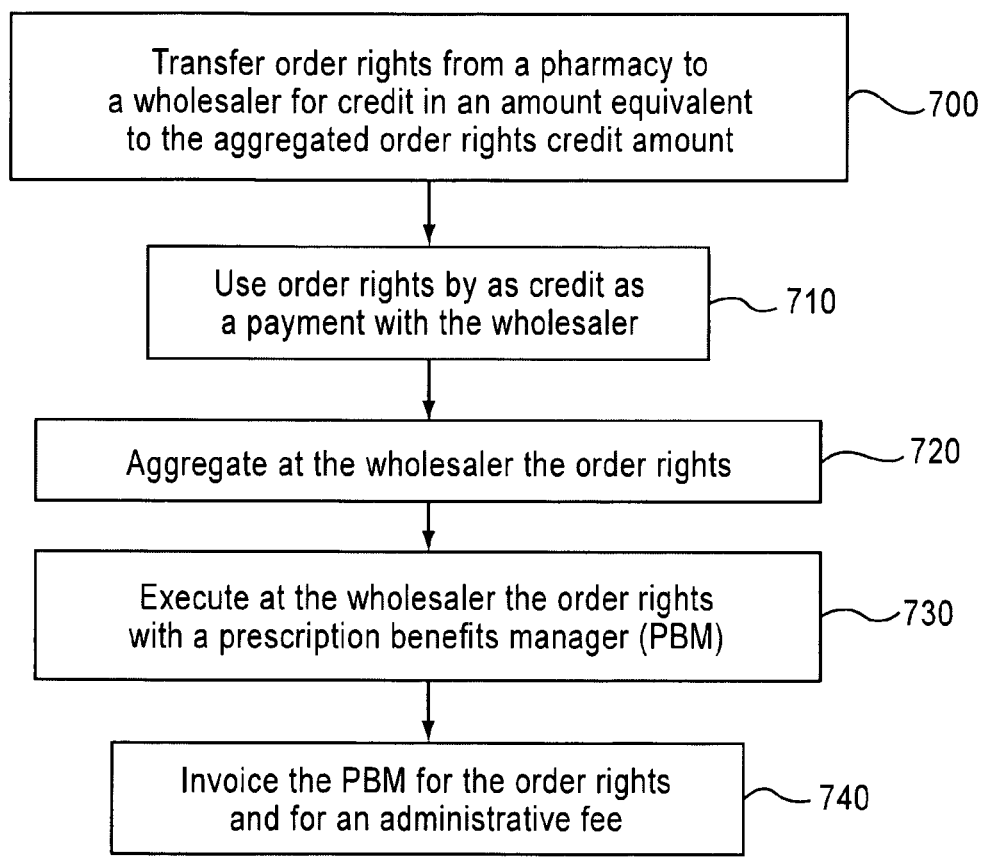
FIG. 10 illustrates an aggregated order rights process, in accordance with an alternative embodiment of the present invention.

After step 260 of FIG. 4, the processes illustrated and described in FIGS. 10 and 11 for the alternative embodiment of the present invention, may be executed or performed simultaneously or sequentially.

FIG. 10 illustrates an aggregated order rights process, in accordance with an alternative embodiment of the present invention. Upon dispensing the prescription to the patient 10 (after step 260 of FIG. 4), in the aggregated order rights process, at step 700, the pharmacy 20 may transfer the order rights to the wholesaler or chain headquarters 50 for credit in an amount equivalent to the aggregated order rights credit amount. At step 710, the pharmacy 20 may elect to use the order rights as credit as a payment with the wholesaler 50 upon dispensing of the prescription drug the pharmacy's next prescription drug order (often daily). At step 720, the wholesaler 50 may aggregate the order rights transferred from the pharmacy 20.

At step 730, the wholesaler 50 executes or uses the order rights with the PBM 40. At step 740, the wholesaler 50 invoices the PBM 40 for the entire order rights. The wholesaler 50 may also invoice the PBM 40 for the administrative fee associated with the order rights and order rights credit amount.

FIG. 11 illustrates an invoice and replenishing process, in accordance with an embodiment of the present invention. Upon dispensing the prescription to the patient 10 (after step 260 of FIG. 4), at step 800, the PBM 40 transmits the claim adjudication response to the payer 80 and invoices the payer 80 for the dispensing fee for the pharmacy 20 associated with the claim adjudication response.

At step 810, the payer 80 submits the payment for the dispensing fee to the PBM 40 and transmits eligibility files to the PBM 40. At step 820, the PBM 40 receives the payment for the dispensing fee from the payer 80. At step 830, the pharmacy 20 receives the dispensing fee from the PBM 40.

At step 840, pharmacy 20 submits the order rights for credit to the wholesaler 50. At step 850, the wholesaler 50 maintains records for the credit in order to be applied as payment for future orders from the pharmacy 20. At step 860, the wholesaler 50 executes the order rights, individually or aggregated, with the PBM 40. At step 870, the PBM 40 invoices the payer 80 for the order rights credit amount, the dispensing fee, and the administrative fee for the wholesaler 50.

At step 880, the payer 80 submits the payment for the order rights credit amount and the administrative fee to the PBM 40. At step 890, the PBM 40 receives the payment and forwards the payment to the wholesaler 50.

Therefore, in accordance with an alternative embodiment of the present invention, rather than being replenished for any prescription drugs dispensed to a patient, the pharmacy may elect to transfer the order rights to a wholesaler who originally supplied the prescription drugs dispensed or any other participating wholesaler for credit in an amount equivalent to an aggregated amount of the order rights. A health provider (PBM), in accordance with an embodiment of the present invention would maintain order rights account for each participating pharmacy and wholesaler and monitor and record the execute and transfer of order rights from pharmacies to wholesalers.

Some of the many advantages of the present invention include to compensate for the services provided, the healthcare provider (PBM) may pay the pharmacy a higher dispensing fee than current health care systems. Also, the healthcare provider (PBM) may pay the wholesaler administrative fee for filling orders from pharmacies, for receiving order rights, and for invoicing a payer, such as the Department of Defense, or TMA for reimbursement of the administrative fee. The payer or TMA would pay the healthcare provider (PBM) for managing the order rights system. In the commercial context, the new embodiments described above would improve transparency because the negotiation of the purchase price of the drug would be between the PBM (or the purchasing insurer) and the manufacturer with no need for a rebate mechanism.

The configuration shown in FIGS. 1 and 7 of information sharing between the pharmacy 20, the PBM 40, the wholesaler 50, the payer 80, the prime vendor 90, and the manufacturer 100 are for purposes of illustration and are by no means exhaustive. In addition, as will be apparent to one of ordinary skill in the art, though the invention is described with reference to specific examples, the hardware, software and location functions can be easily modified.

It is to be understood that in the embodiment of the present invention, the steps are performed in the sequence and manner as shown although the order of some steps and the like may be changed without departing from the spirit and scope of the present invention. In addition, the methods described in FIGS. 4-6 and 10-11 may be repeated as many times as needed. Furthermore, although one pharmacy, one wholesaler, and one manufacturer are illustrated and described, a person of ordinary skill in the art will appreciate that multiple pharmacies may be operatively connected to a single or multiple wholesalers. Also, a person of ordinary skill in the art will appreciate that multiple wholesalers may be operatively connected to a single or multiple manufacturers.

Each of the subsystems may be implemented by hardware and/or software components. Further, each of the subsystems can reside on both hardware and software components. Certain functionalities can be unique to a subsystem in some cases but in many cases several subsystems possess identical functionalities. Additionally, subsystems and functionalities can be duplicated on different parts of the system.

Some subsystems can be comprised only of software modules that reside on system hardware. For such subsystems, functionality is primarily provided by the software modules. Other subsystems can be comprised of software modules and specific electronic hardware components. Specific hardware components can include but are not limited to, an apparatus for containing and/or dispensing medication; a computer network; a server; a personal computer, laptop, handheld or equivalent; a dumb terminal; or a combination of these components. The functionalities of such subsystems may be provided by both the physical characteristics of the hardware and the software modules that enable it to perform its specific tasks.

In accordance with an embodiment of the present invention, a computer program embodied on a computer-readable medium may also be provided, encoding instructions for performing at least the method described in FIGS. 4-6 and 10-11, in accordance with an embodiment of the present invention.

The computer program product can be implemented in hardware, software, or a hybrid implementation. The computer program product can be composed of modules that are in operative communication with one another, and which are designed to pass information or instructions to a communications device such as a user equipment or network node. The computer program product can be configured to operate on a general purpose computer or an application specific integrated circuit (ASIC).

The subsystems can utilize one or more computers. As used herein computer, including a user computer, cabinet controllers and the computers comprising servers, can be any microprocessor or processor controlled device that permits access to the Internet, including terminal devices, such as personal computers, workstations, servers, clients, mini computers, main-frame computers, laptop computers, a network of individual computers, mobile computers, palm-top computers, hand-held computers, set top boxes for a TV, interactive televisions, interactive kiosks, personal digital assistants, interactive wireless communications devices, mobile browsers, or a combination thereof. The computers can further possess input devices such as a keyboard, mouse, touchpad, joystick, pen-input-pad, output devices such as a computer screen and a speaker, fingerprint readers, touchscreens, label printers, and the like.

These computers may be uni-processor or multi-processor machines. Additionally, these computers include an addressable storage medium or computer accessible medium, such as random access memory (RAM), an electronically erasable programmable read-only memory (EEPROM), programmable read-only memory (PROM), erasable programmable read-only memory (EPROM), hard disks, floppy disks, laser disk players, digital video devices, compact disks, video tapes, audio tapes, magnetic recording tracks, electronic networks, and other techniques to transmit or store electronic content such as, by way of example, programs and data. The computers can be equipped with a network communication device such as a network interface card, a modem, or other network connection device suitable for connecting to a networked communication medium.

Furthermore, the computers may execute an appropriate operating system such as Linux, Unix, Microsoft® Windows®, Apple® MacOS®, or IBM® OS/2®. The appropriate operating system may include a communications protocol implementation which handles all incoming and outgoing message traffic passed over the Internet. While the operating system may differ depending on the type of computer, the operating system can continue to provide the appropriate communications protocols necessary to establish communication links with the Internet.

The computers may include program logic, or other substrate configuration representing data and instructions, which cause the computer to operate in a specific and predefined manner as described herein. The program logic may be implemented as one or more modules. The modules may be configured to reside on the addressable storage medium and configured to execute on one or more processors. The modules include, but are not limited to, software or hardware components which perform certain tasks. Thus, the pharmacy, the prescription benefits manager (PBM), the wholesaler or chain headquarters, the payer, the prime vendor, and the manufacturer, each previously described, may include, by way of example, components, such as, software components, object-oriented software components, class components and task components, processes, functions, attributes, procedures, subroutines, segments of program code, drivers, firmware, microcode, circuitry, data, databases, data structures, tables, arrays, and variables.

"Internet" refers to a network or combination of networks spanning any geographical area, such as a local area network, wide area network, regional network, national network, and/or global network. As used herein, "Internet" may refer to hardwire networks, wireless networks, or a combination of hardwire and wireless networks. Hardwire networks may include, for example, fiber optic lines, cable lines, ISDN lines, copper lines, etc. Wireless networks may include, for example, cellular systems, personal communication services (PCS) systems, satellite communication systems, packet radio systems, and mobile broadband systems. A cellular system may use, for example, code division multiple access (CDMA), time division multiple access (TDMA), personal digital phone (PDC), Global System Mobile (GSM), or frequency division multiple access (FDMA), among others.

In addition, while the term information has been used in the description of the present invention, the invention has import to many types of network information. For purposes of this invention, the term information includes data, packets, cells, frames, datagrams, bridge protocol data unit packets, packet data and any equivalents thereof.

The many features and advantages of the invention are apparent from the detailed specification and, thus, it is intended by the appended claims to cover all such features and advantages of the invention which fall within the true spirit and scope of the invention. Further, since numerous modifications and changes will readily occur to those skilled in the art, it is not desired to limit the invention to the exact construction and step illustrated and described, and accordingly all suitable modifications and equivalents may be resorted to, falling within the scope of the invention.

What is claimed:

1. An apparatus, comprising:
   a receiver configured to receive and process a claim adjudication request;
   a processor configured to grant an order right to a pharmacy based on the claim adjudication request, wherein the order right comprises a right assigned to the pharmacy to have a prescription drug dispensed replenished;
   an output unit configured to output a claim adjudication response and the order right to a payer, and configured to output a dispensing fee to the pharmacy for dispensing a prescription drug to a patient; and
   a controller configured to execute the order right with a wholesaler to replenish the prescription drug dispensed at no cost to the pharmacy.

2. The apparatus as recited in claim 1, wherein the receiver is further configured to receive an invoice from the wholesaler for an administrative fee for replenishing the prescription drug at no cost to the pharmacy.

3. The apparatus as recited in claim 1, wherein the controller processes the claim adjudication request in real time.

4. The apparatus as recited in claim 2, wherein the output unit is further configured to transmit an invoice to the payer for total charges of the order right, comprising data representative of the administrative fee for the wholesaler and the data representing the dispensing fee, and the receiver is configured to receive a payment for the total charges and eligibility files from the payer.

5. The apparatus as recited in claim 1, wherein the apparatus comprises a prescription benefits manager.

6. An apparatus, comprising:
a receiver configured to receive an order right from a pharmacy, wherein the order right comprises a right assigned to the pharmacy to have a prescription drug dispensed replenished;
a controller configured to replenish the pharmacy with the prescription drug dispensed at no cost to the pharmacy; and
a processor configured to process the order right to invoice a prescription benefits manager for an administrative fee to compensate for replenishing the prescription drug at no cost to the pharmacy.

7. The apparatus as recited in claim 6, wherein the controller is further configured to aggregate a predetermined number of order rights at predefined time intervals for a number of patients, or in redefined order quantities.

8. The apparatus as recited in claim 6, wherein the apparatus comprises a server in a wholesaler.

9. A system, comprising:
a prescription benefits manager configured to receive a claim adjudication request from a pharmacy for a prescription drug dispensed, output a claim adjudication response, and generate an assignment of order rights to the pharmacy based on the claim adjudication request, wherein the order rights comprise rights assigned to the pharmacy to have a prescription drug dispensed replenished; and
a wholesaler configured to receive the order rights from the pharmacy, aggregate the order rights up to order rights quantities, execute the aggregated order rights with the prescription benefits manager, and replenish the drugs at no cost to the pharmacy.

10. The system as recited in claim 9, wherein the pharmacy is configured to aggregate a predetermined number of order rights either at predefined time intervals, associated with a particular wholesaler, a predetermined number of patients, or in predefined order quantities.

11. The system as recited in claim 9, wherein the claim adjudication response comprises total charges associated with the prescription drug dispensed including a patient's co-pay and a dispensing fee for the pharmacy for dispensing the prescription drug.

12. The system as recited in claim 9, wherein the wholesaler invoices the prescription benefits manager for an administrative fee to compensate the wholesaler for replenishing the pharmacy at no cost.

13. The system as recited in claim 9, upon dispensing the prescription to the patient, the prescription benefits manager is further configured to transmit the claim adjudication response, transfer the order rights, and invoice the payer for the total charges to process the aggregated order rights, including the administrative fee for the wholesaler and the dispensing fee for the pharmacy associated with the claim adjudication response.

14. The system as recited in claim 13, wherein the payer submits the payment for the total charges to the prescription benefits manager.

15. The system as recited in claim 13, wherein, in the transfer of the order rights, the prescription benefits manager provides information, such as quantity of the drugs dispensed based on the aggregated order rights and identification of the wholesaler to the payer.

16. The system as recited in claim 9, wherein the prescription benefits manager receives the payment for the total charges from the payer and transmits the administrative fee to the wholesaler.

17. The system as recited in claim 9, wherein the payer is configured to provide ordering and sorting of the information, comprising a quantity of prescription drugs dispensed and an identification of the wholesaler to be replenished by a drug manufacturer.

18. A method, comprising:
receiving and processing, using a receiver, a claim adjudication request;
granting, using a processor, an order right to a pharmacy based on the claim adjudication request, wherein the order right comprises a right assigned to the pharmacy to have a prescription drug dispensed replenished;
outputting, using an output unit, a claim adjudication response and the order right to a payer;
outputting, using the output unit, data representing a dispensing fee for the pharmacy for dispensing a prescription drug to a patient; and
executing, using a controller, the order right with a wholesaler to replenish the prescription drug dispensed at no cost to the pharmacy.

19. The method as recited in claim 18, further comprising:
receiving an invoice from the wholesaler for an administrative fee for replenishing the prescription drug at no cost to the pharmacy.

20. The method as recited in claim 18, further comprising:
performing the processing of the claim adjudication request in real time.

21. The method as recited in claim 18, further comprising:
transmitting an invoice to the payer for total charges of the order right, comprising data representative of the administrative fee for the wholesaler and the data representing the dispensing fee; and receiving a payment for the total charges and eligibility files from the payer.

22. A method, comprising:
receiving, using a receiver an order right from a pharmacy, wherein the order right comprises a right assigned to the pharmacy to have a prescription drug dispensed replenished;
replenishing, using a controller, the pharmacy with the prescription drug dispensed at no cost to the pharmacy; and
processing, using a processor, the order right to invoice a prescription benefits manager for an administrative fee to compensate a wholesaler for replenishing the prescription drug at no cost to the pharmacy.

23. The method as recited in claim 22, further comprising:
aggregating a predetermined number of received order rights at predefined time intervals, associated with the wholesaler, for a number of patients, or in predefined order quantities.

24. A computer program embodied on a computer readable medium, the computer program being configured to control a processor to perform:
receiving and processing a claim adjudication request;
granting an order right to a pharmacy based on the claim adjudication request, wherein the order right comprises a right assigned to the pharmacy to have a prescription drug dispensed replenished;
outputting a claim adjudication response and the order right to a payer and data representing a dispensing fee for the pharmacy for dispensing a prescription drug; and
executing the order right with a wholesaler to replenish the prescription drug dispensed at no cost to the pharmacy.

25. An apparatus, comprising:
a receiver configured to receive and process a claim adjudication request;
a processor configured to grant an order right to a pharmacy based on the claim adjudication request, wherein the order right comprises a right assigned to the pharmacy to have a prescription drug dispensed replenished;

an output unit configured to output a claim adjudication response and an invoice to a payer for total charges of the order right, wherein the total charges comprise an order right credit amount, an administrative fee for a wholesaler, and a dispensing fee to the pharmacy for dispensing the prescription drug, wherein the order rights credit amount is an amount to be granted to the wholesaler for providing credit to the pharmacy for the order right; and a controller configured to transmit the administrative fee and order rights credit amount to the wholesaler.

26. The apparatus as recited in claim 25, wherein the receiver is configured to receive a payment for the total charges and eligibility files from the payer.

27. The apparatus as recited in claim 25, wherein upon receipt of the administrative fee and the order rights credit amount from the payer, the output unit is configured to transfer the administrative fee and the order rights credit amount to the wholesaler and configured to transfer the dispensing fee to the pharmacy.

28. The apparatus as recited in claim 25, wherein the apparatus comprises a prescription benefits manager.

29. An apparatus, comprising:
a receiver configured to receive an order right from a pharmacy, wherein the order right comprises a right assigned to the pharmacy to have a prescription drug dispensed replenished;

a controller configured to aggregate a predetermined number of order rights at predefined time intervals in predefined order quantities, configured to execute the aggregated order rights with a prescription benefits manager, and configured to provide the prescription drug requested by the pharmacy against the credit; and a processor configured to invoice the prescription benefits manager for the aggregated order rights associated with the dispensed orders from the pharmacy and for an administrative fee associated with the providing of the prescription drug to the pharmacy for credit.

30. The apparatus as recited in claim 29, wherein the apparatus comprises a wholesaler.

31. A system, comprising:
a prescription benefits manager configured to receive a claim adjudication request from a pharmacy for a prescription drug dispensed, output a claim adjudication response, and generate an assignment of order rights to the pharmacy based on the claim adjudication request, wherein the order rights comprise rights assigned to the pharmacy to have a prescription drug dispensed replenished; and a wholesaler configured to receive the order rights from the pharmacy for credit in an amount equivalent to the amount of the order rights, aggregate the order rights up to order rights quantities, execute the aggregated order rights with the prescription benefits manager, and provide the prescription drug requested by the pharmacy against the credit.

32. The system as recited in claim 31, wherein the pharmacy is configured to aggregate a predetermined number of order rights either at predefined time intervals, associated with a particular wholesaler, a predetermined number of patients, or in predefined order quantities.

33. The system as recited in claim 31, wherein the claim adjudication response comprises total charges associated with the prescription drug dispensed including a patient's co-pay and a dispensing fee for the pharmacy for dispensing the prescription drug.

34. The system as recited in claim 31, wherein the wholesaler is further configured to invoice the prescription benefits manager for the aggregated order rights associated with the dispensed orders from the pharmacy and for an administrative fee associated with the replacement of prescription drug to the pharmacy for credit.

35. The system as recited in claim 34, wherein the prescription benefits manager is further configured to output a claim adjudication response and an invoice to a payer for total charges of the order right, wherein the total charges comprise an order right credit amount, an administrative fee for a wholesaler, and a dispensing fee to the pharmacy for dispensing the prescription drug, wherein the order rights credit amount is an amount to be granted to the wholesaler for providing credit to the pharmacy for the order right.

36. The system as recited in claim 35, wherein the prescription benefits manager is further configured to transmit the administrative fee and order rights credit amount to the wholesaler.

37. The system as recited in claim 36, wherein, in the transfer of the order rights, the prescription benefits manager is further configured to provide quantity of prescription drugs dispensed by the pharmacy based on the aggregated order rights and identification of the wholesaler to the payer.

38. A method, comprising:
receiving and processing, using a receiver, a claim adjudication request; granting, using a processor, an order right to a pharmacy based on the claim adjudication request, wherein the order right comprises a right assigned to the pharmacy to have a prescription drug dispensed replenished;

outputting, using an output unit, a claim adjudication response and an invoice to a payer for total charges of the order right, wherein the total charges comprise an order right credit amount, an administrative fee for a wholesaler, and a dispensing fee to the pharmacy for dispensing the prescription drug, wherein the order rights credit amount is an amount to be granted to the wholesaler for providing credit to the pharmacy for the order right; and transmitting, using a controller, the administrative fee and order rights credit amount to the wholesaler.

39. The method as recited in claim 38, further comprising: receiving a payment for the total charges and eligibility files from the payer.

40. The method as recited in claim 38, wherein upon receipt of the administrative fee and the order rights credit amount from the payer, the method further comprises: transferring the administrative fee and the order rights credit amount to the wholesaler and transferring the dispensing fee to the pharmacy.

41. A method, comprising:
receiving, using a receiver an order right from a pharmacy, wherein the order right comprises a right assigned to the pharmacy to have a prescription drug dispensed replenished;

aggregating, using a controller, a predetermined number of order rights at predefined time intervals in predefined order quantities;

executing, using the controller, the aggregated order rights with a prescription benefits manager;

providing, using the controller, the prescription drug requested by the pharmacy against the credit; and invoicing, using a processor, the prescription benefits manager for the aggregated order rights associated with the dispensed orders from the pharmacy and for an administrative fee associated with the providing of the prescription drug to the pharmacy for credit.

42. A computer program embodied on a computer readable medium, the computer program being configured to control a processor to perform:
- receiving and processing a claim adjudication request;
- granting an order right to a pharmacy based on the claim adjudication request, wherein the order right comprises a right assigned to the pharmacy to have a prescription drug dispensed replenished;
- outputting a claim adjudication response and an invoice to a payer for total charges of the order right, wherein the total charges comprise an order right credit amount, an administrative fee for a wholesaler, and a dispensing fee to the pharmacy for dispensing the prescription drug, wherein the order rights credit amount is an amount to be granted to the wholesaler for providing credit to the pharmacy for the order right; and
- transmitting the administrative fee and order rights credit amount to the wholesaler.

* * * * *